United States Patent [19]

Ragozin et al.

[11] Patent Number: 5,687,731
[45] Date of Patent: Nov. 18, 1997

[54] OSCILLOMETRIC METHOD FOR DETERMINING HEMODYNAMIC PARAMETERS OF THE ARTERIAL PORTION OF PATIENT'S CIRCULATORY SYSTEM AND A MEASURING SYSTEM FOR ITS REALIZATION

[75] Inventors: Viacheslav Nikolaievich Ragozin; Vladimir Alexandrevitch Degtiarev, both of Moscow, Russian Federation

[73] Assignee: MTI, Ltd., Tortola, Virgin Islands (Br.)

[21] Appl. No.: 336,020

[22] Filed: Nov. 8, 1994

Related U.S. Application Data

[63] Continuation of Ser. No. 115,150, Sep. 2, 1993, abandoned.

[30] Foreign Application Priority Data

| Sep. 10, 1992 | [RU] | Russian Federation | 5056329 |
| Sep. 10, 1992 | [RU] | Russian Federation | 5056330 |
| Sep. 10, 1992 | [RU] | Russian Federation | 5056331 |

[51] Int. Cl.$^6$ .................................... A61B 5/022
[52] U.S. Cl. .................. 128/672; 128/680; 128/691; 128/713
[58] Field of Search .................. 128/672, 677, 128/679, 680-6, 688

[56] References Cited

U.S. PATENT DOCUMENTS

| 4,331,156 | 5/1982 | Apple et al. | 128/688 |
| 4,484,584 | 11/1984 | Uemura | 128/680 |
| 4,638,810 | 1/1987 | Ramsey, III et al. | 128/681 |
| 4,651,747 | 3/1987 | Link | 128/677 |
| 4,703,760 | 11/1987 | Miyawaki et al. | 128/681 |
| 4,800,892 | 1/1989 | Perry et al. | 128/679 |
| 4,922,918 | 5/1990 | Ruiter | 128/680 X |
| 4,995,399 | 2/1991 | Hayashi et al. | 128/680 |
| 5,031,631 | 7/1991 | Kawamura et al. | 128/685 |
| 5,054,494 | 10/1991 | Lazzaro et al. | 128/677 |
| 5,170,795 | 12/1992 | Ramsey, III et al. | 128/680 X |
| 5,172,696 | 12/1992 | Souma | 128/672 |
| 5,267,567 | 12/1993 | Aung et al. | 128/680 |

FOREIGN PATENT DOCUMENTS

| 0145208 | 6/1985 | European Pat. Off. . |
| 1036318 | 8/1983 | U.S.S.R. . |
| 1230588 | 5/1986 | U.S.S.R. . |
| 1308316 | 5/1987 | U.S.S.R. . |

OTHER PUBLICATIONS

N.N. Savitsky—The Biophysical Foundation of Blood Circulation and Clinical Methods of the Study of Hemodynamics, pp. 138 to 151 (Leningrad, Russia 1974).

*Primary Examiner*—Lee S. Cohen
*Assistant Examiner*—Bryan K. Yarnell
*Attorney, Agent, or Firm*—Felfe & Lynch

[57] ABSTRACT

An oscillometric method for determining hemodynamic parameters of the arterial portion of patient's circulatory system, consisting in recording the pulse pressure waves in the major arterial vessel under examination, under the effect of a linearly varying pressure in a pneumatic vessel-constricting pressure cuff, with the result that a closed contour is formed within a single measuring cycle, which is established by straight lines the points of intersection of which are the signs of arterial pressure, while the amplitude values of the pulse waves in the contour determine the geometric parameters of the major arterial vessel under examination. A measuring system for carrying the method into effect features a linear characteristic of conversion and a straight horizontal amplitude-frequency characteristic in a frequency range of approximately from 0 to 50 Hz along a through path of conversion, amplification, and recording.

46 Claims, 7 Drawing Sheets

B - 75mm Hg
C - 95mm Hg
F - 120mm Hg
K - 135mm Hg

OSCILLOMETRIC METHOD FOR DETERMINING HEMODYNAMIC PARAMETERS OF THE ARTERIAL PORTION OF PATIENT'S CIRCULATORY SYSTEM AND A MEASURING SYSTEM FOR ITS REALIZATION

This application is a continuation of application Ser. No. 08/115,150, filed Sep. 2, 1993 now abandoned.

FIELD OF THE INVENTION

The present invention relates to medicine and has particular reference to physiology and cardiology; it can find application in clinical and experimental studies as a noninvasive method for diagnosis of the state of the circulatory system.

PROBLEMS TO BE SOLVED

An ever-increasing incidence of cardiovascular diseases necessitates rapid and reliable patients' examination for detecting and preventing even minute deviations from the norm of a sound human being. With the above problem in view, an examination method is required with is capable of yielding quite a number of parameters for a short period of time, characteristic of the state of human circulatory system without causing any emotional stress therein that could affect the examination results. To this end, the method must be noninvasive and a negative effect exerted upon the patient be minimized. Such a method can find application in diagnosis and treatment of hypotensive and hypertensive diseases, in circulatory insufficiency, and in some other widespread cardiovascular diseases.

BACKGROUND OF THE INVENTION

There are known at present a number of noninvasive methods for measuring the circulatory system parameters. One of such methods developed under the egis of the firm Pulse Metric, Inc. (the instrument 200M DYNAPULSE™), consists in that an oscillometric curve of arterial pulse is registered by the measuring system, the curve resulting from the effect of a decreasing pressure in the cuff that builds up the pressure applied to the great arterial vessel being examined. The data obtained makes it possible ti measure the diastolic, systolic, and mean arterial pressure, as well the pulse rate of the patient under examination. The oscillometric curve and the measurement results are displayed on the screen of a monitor and the findings can be written in the memory of a personal computer or on a "personal health diskette" of the patient under examination. The measuring system consists of a pressure measuring cuff which is manually inflated, a signal converter, amplifiers, and a logic circuit.

The oscillometric curve of arterial pulse as recorded by the Pulse Metric, Inc. instrument demonstrates that the amplitude-frequency characteristic of the measuring system converts the volume pulse signals of the arterial pulse into signals close to the rate-of-change signals. As a result, formation of arterial pressure parameters is time-shifted and error of their measurement is increased. But the key point resides in that the amplitude values of the registered pulse waves lose information about the volume being measured, since they bear information about the rate of change of the volume. That is why the amplitude values cannot be employed for obtaining the data on the cross-sectional area of the major arterial vessel under examination nor can one judge on its hydrodynamic characteristics.

One more prior-art noninvasive method is known under the title of "Method and apparatus for determining blood pressure and cardiovascular condition" (cf. U.S. Pat. No. 4,880,013 issued Nov. 14, 1989). According to said method, there are determined the following three parameters, that is, the diastolic, the mean dynamic, and the systolic arterial pressure. When registering an oscillometric curve use is made of pressure reduction in the cuff, and the measuring system converts the volume signals of the pulse waves into signal close to the velocity signals.

However, even the method fails to provide a reliable information about the arterial pressure parameters and on a change in the cross-sectional area of the major arterial vessel under examination.

Also known in the art presently is a tacho-oscillographic method for measuring arterial pressure developed by N. N. Savitski as disclosed in his monography entitled "Biophysical fundamentals of circulation and clinical methods for study of hemodynamics", 1974, Leningrad, Meditsina Publishers, pp. 141–150 (in Russian). The method is also based on measurement changes in the volume of the patient's limb vessel being examined, which changes are liable to occur under the effect of throbbing blood stream flow along the major blood vessels. The method is capable of measuring the diastolic, mean dynamic, lateral systolic, and end systolic arterial pressure in the major blood vessel of the limb to which a measuring vessel-constricting cuff is applied. The arterial pressure parameters are determined while the pressure in the cuff is being raised, since it is considered that in this case linearity of pressure variation can be ensured more readily.

The measuring system for registering tacho-oscillograms comprises pneumatic and electronic units. Used as a converter is a differential air pressure gauge, and the curve is recorded on a photographic paper.

The method discussed above suffers from a number of instrumental and methodical errors.

The basic instrumental error is determined by the measuring system and appears as a result of the linear conversion of the low-frequency portion (from 0 to 1.5–5 Hz) of the volume oscillometric signal sensed by the measuring cuff from the major limb arterial vessel, into velocity rate signals. This results in a phase (time) shift of the arterial pressure parameters during their formation on an oscillometric curve and hence in arterial pressure measurement errors.

The principal methodical (human) error of the tacho-oscillographic method resides in a subjective approach to decoding of the data obtained in determining the signs of pressure. The amount of total methodical error in absolute values cannot be evaluated, though practice demonstrates that the spread in the measured values of arterial pressure during decoding tacho-oscillograms ranges approximately from 10 to 15 mm Hg.

Thus, none of the afore-discussed methods, when carried into effect with the aid of their own measuring systems, can represent real processes occurring in an arterial vessel under the action of a variable pressure in the measuring cuff. In this case, the signals being registered bear more information about the rate of change of the volume of the major arterial vessel under examination. Thus, the error of determination of arterial pressure parameters is increased, there is impossible to calculate the geometric parameters of the vessel involved and its hemodynamic characteristics and, eventually, the amount of information obtained is decreased and reliability of the diagnosis of the state of the circulatory system in the patient under examination is badly affected as a whole.

SUMMARY OF THE INVENTION

In keeping with the foregoing, the invention has for its principal object to provide a noninvasive method for determining hemodynamic parameters of the arterial portion of the circulatory system for making a reliable diagnosis of the state of the cardiovascular system of the patient under examination according to many parameters.

It is an extremely important object of the present invention to provide a measuring system for converting, amplifying, and recording real arterial pulse signals involving minimal frequency and phase distortions.

It is not a less important object of the present invention to provide a physiologically substantiated oscillometric method for determining the hemodynamic parameters of the arterial portion of the patient's circulatory system, which confirms the correctness of forming an oscillometric curve of the arterial pulse, enabling one to obtain information about the state of the cardiovascular system with a high degree of reliability.

It is an additional object of the proposed invention to provide a simple retrieval of information from a single measuring cuff applied to the patient's limb major vessel under examination.

It is one more extremely important object of the present invention to provide an oscillometric method and a measuring system which are capable of obtaining maximum high-accuracy information about only the parameters of the arterial vessels and the heart, but also on their hemodynamic interaction.

It is another important object of the present invention to provide an oscillometric method for determining the hemodynamic parameters of the arterial portion of the circulatory system enabling one to obtain an oscillometric curve of the arterial pulse having individual features characteristic of every patient under examination.

It is a further important object of the present invention to provide a method for determining the hemodynamic parameters of the arterial portion of the circulatory system that makes it possible to obtain information about not only the arterial pressure parameters, but also on the characteristic of the blood stream running along the major arterial vessel under examination.

It is still a further object of the present invention to provide a method capable of not only determining the hemodynamic parameters of the arterial portion of the circulatory system, but also of obtaining information about the geometric parameters of the major arterial pressure under examination and on its tonus.

It is a substantially important object of the present invention to provide a method for determining the hemodynamic parameters of the arterial portion of the circulatory system which makes it possible to utilize the heretofore-known hydrodynamic formulas to considerably extend the scope and reliability of the information obtained.

It is one more object of the present invention to provide a method for obtaining an oscillometric curve and a measuring system for its realization, in which the curve enables one to diagnose a change in the state of the patient's cardiovascular system merely against a change in the appearance of the curve.

It is still another important object of the present invention to provide such a method for determining the hemodynamic parameters of the arterial portion of the circulatory system that is not causative of an emotional response in the patient under examination capable of changing the status of his cardiovascular system.

It is yet still another important object of the present invention to provide such an oscillometric method for determining the hemodynamic parameters of the arterial portion of the circulatory system and a measuring system for its realization that enable unskilled medical personnel to be engaged in patients' examination.

It is a further object of the present invention to provide a measuring system for determining the hemodynamic parameters of the arterial portion of the patient's circulatory system, based on the heretofore known extensively applicable electronic and mechanical units and components.

It is an additional object of the present invention to provide a method and a measuring system for determining the hemodynamic parameters of the arterial portion of the patient's circulatory system, wherein formation of an oscillometric curve makes it possible to automate the processing of the results of measuring the hemodynamic parameters of the circulatory system in the patient under examination.

With the foregoing and further objects of the present invention the essence of the proposed method for determining the hemodynamic parameters of the arterial portion of the circulatory system of the patient under examination consists in that when using a measuring system featuring a linear conversion characteristic and a straight horizontal amplitude-frequency characteristic in a frequency range from about 0 to 50 Hz throughout the path of conversion, amplification, and recording of volume signals of the pulse waves and application of a linearly increasing pressure in the pneumatic vessel-constricting pressure cuff, there are registered virtually real (genuine) volume oscillometric signals which represent completely the correctness of the process proceeding in forming oscillograms of arterial vessels under the action of a linearly rising pressure in the pneumatic vessel-constricting pressure cuff and retains the amplitude-time relationships undistorted. As a result, the oscillometric curve of the arterial pulse acquires an appearance of a regularly developing contour, wherein the interaction between the linearly variable pressure in the cuff and the pulsating pressure in the major arterial vessel under examination establishes reliably the signs of the arterial pressure, while each pulse wave bears information on volume changes occurring in the vessel involved.

BRIEF DESCRIPTION OF THE DRAWINGS

In what follows the herein-disclosed oscillometric method for determining the hemodynamic parameters of the arterial portion of the patient's circulatory system and the measuring system realizing the method are illustrated in some specific exemplary embodiments of the invention to be read with reference to the appended drawings, wherein.

BEST METHOD OF CARRYING OUT THE INVENTION

The herein-disclosed oscillometric method for determining the principal parameters of the arterial portion of the circulatory system is as follows.

Figure 1:
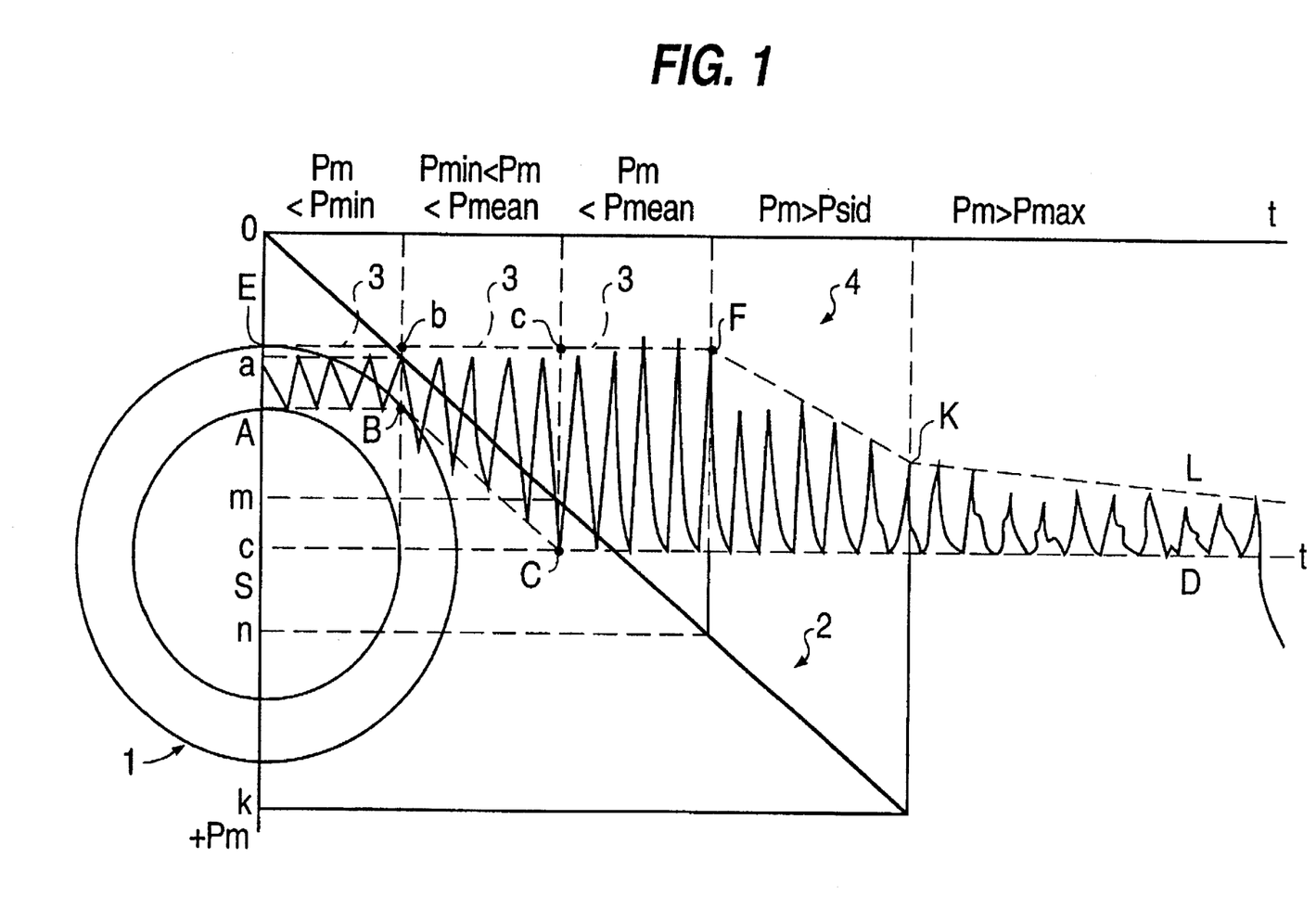
FIG. 1 is a schematic view of changes in the cross-section the major arterial vessel under examination due to both the pulsing blood flow and the increasing pressure in the cuff. In accordance with the invention, this interaction develops into a volume oscillometric curve of the arterial pulse corresponding to the changes in the volume of the vessel.

A pneumatic pressure cuff (omitted in FIG. 1) is applied to a major arterial vessel 1 (FIG. 1) to be examined which runs along either of the limbs of the patient under examination, whereupon a linearly variable pressure is built up in the cuff for about 40–60 seconds, the pressure varying approximately within 0 and 300 mm Hg (a straight line 2 in FIG. 1). Then the signals of pulse waves 3 picked off the cuff, are recorded with the aid of the measuring system (FIG. 7) featuring a linear conversion characteristic and a straight horizontal amplitude-frequency characteristic in a frequency range of approximately from 0 to 50 Hz to obtain an oscillometric curve 4 of the arterial pulse. The pulse waves 3 thus recorded represent a change in the volume of the vessel 1 depending on the pulsating blood stream running therealong.

Thus, the oscillometric curve 4 of the arterial pulse is formed under the effect of a linearly rising pressure in the cuff, the absolute values of the pressure being registered simultaneously with the pressure signals of the pulse waves 3. Then the diastolic region indicated with the letters ABCD (FIG. 1) and the systolic region indicated with the letters EFKL are recognized in the thus-obtained oscillometric curve 4, whereupon extreme points are discriminated in the region which belong simultaneously to both of them, i.e., the points ABCD in the diastolic region and the points EFKL in the systolic region. Next the straight lines AB, BC, CD are drawn through the aforestated extreme points in the diastolic region, and the straight lines EF, FK, KL are drawn in the systolic region. The aforementioned straight lines are drawn until they intersect in the regions, thus producing a virtually closed contour AEFKLDCBA bounded from left and right by the coordinate of the development time of the oscillometric curve 4. The points of intersection of the straight lines AB, BC, and CD, as well as EF, FK and KL correspond to the arterial pressure parameters being measured.

The principle of measurement of the arterial pressure parameters is based on comparison of the instantaneous values of the pressure in the vessel 1 under examination and of the rising pressure (the straight line 2) in the pneumatic vessel-constricting pressure cuff, the absolute value of the latter pressure being simultaneously recorded on the arterial pulse oscillometric curve 4. Results of measurement of the parameters of one arterial pressure of another that appear on the curve 4 within a measuring cycle are projected onto the running values of the pressure in the cuff (that is, onto the straight line 2), and their values are determined at the projection points.

The sense itself of volume registration of the oscillometric curve 4 consists in the nature of signals converted by the cuff, since the pulse waves 3 are nothing but the value of the increment dS of the cross-sectional area of the vessel 1 that appear in the systolic phase, multiplied by the length L of the vessel under the cuff, that is, the increment dV of the volume of the major arterial vessel 2 under examination equals dV=dS·L. The volume of the vessel 1 in the diastolic phase can be represented as the area S of its cross-section multiplied by the length L, that is, V=S·L. FIG. 1 shows schematically a cross-sectional view of the major arterial vessel 1.

Because the vessel length L remains virtually invariable throughout the entire measuring cycle, the amplitude of the pulse waves 3 on the oscillometric curve 4 is directly proportional to the varying cross-sectional area S of the vessel under examination.

FIG. 1 illustrates how the volume oscillometric curve 4 of the arterial pulse is formed, showing that the regular formation of the signs of arterial pressure on the curve is directly concerned with the change of the volume of the major vessel 1 under examination.

As the pressure in the cuff starts to be raised, the patient's limb portion, wherein the vessel to be examined is situated, is compressed, with the result that the pulse waves 3 are somewhat increased as for the amplitude. Since the blood pressure in the arterioles and minor vessels during the diastolic phase in lower than the major vessel 1 during the same phase, formation of the oscillometric curve 4 occurs under the action of the pulsating pressure in said vessel.

The pressure $P_m$ in the pneumatic vessel-constricting pressure cuff gradually rises until reaching the value of the diastolic pressure $P_{min}$ in the arterial vessel. Thenceforth the diastolic portion of the pulse waves 3 deflects downwards following the law of rising pressure in the cuff, since the pressure $P_m$ in the cuff prevents the vessel 1 from getting completely patent in the diastolic phase. However, the next systolic discharge increases the lumen of the vessel 1 to its previous dimensions S+dS, because the value of the side systolic arterial pressure $P_{sid}$ exceeds the pressure $P_m$ in the cuff, i.e., $P_{sid} > P_m$. With the pressure $P_m$ in the cuff (the straight line 2) varying linearly, the ends of the diastolic portions of the pulse waves 3 "fall up on " the straight line (BC in FIG. 1) that deflects the downwards in compliance with the law of rising pressure in the cuff.

Once the pressure $P_m$ in the cuff has reached the value of the means dynamic arterial pressure $P_{mean}$, i.e., $P_m > P_{mean}$ and starts exceeding it, the vessel 1 starts reducing its lumen at the end of the diastolic phase; hence on further decrease in the volume V of the vessel 1 under the cuff occurs. The cross-sectional area S of the vessel 1 under examination equals zero, which is indicated in the oscillometric curve 4 with an inconsiderable in time flattening in the diastolic region ABCD starting from the point C. Once a fresh blood portion has arrive at the beginning of a next systolic phase, the lumen of the vessel 1 reaches its previous value at the pressure $P_{sid}$, since the pressure $P_m$ in the cuff is still lower than the side systolic pressure $P_{sid}$, i.e., $P_m < P_{sid}$. The first maximal pulse wave 3 in the oscillometric curve 4 of the arterial pulse corresponds to the instant mentioned above, the pulse wave being proportional to the sum of the cross-sectional areas S of the vessel 1 in the diastolic phase and the increment dS of the cross-sectional area S of the vessel 1 in the systolic phase, i.e., S+dS.

Further rise of the pressure P in the cuff results in time extension of the aforementioned flattening of the diastolic portion ABCD in the oscillometric curve 4, whereas the amplitudes of the pulse waves 3 retain their value until the pressure $P_m$ in the cuff reaches the value of the side systolic pressure $P_{sid}$ and are arranged on the straight line EF from the beginning of the measuring cycle. The ends of the diastolic sections of the pulse waves 3 in the diastolic region ABCD, starting from the value of the mean dynamic arterial pressure $P_{mean}$ until the end of the measuring cycle, "fall upon" the straight line CD.

Once the pressure $P_m$ in the cuff has become equal to the side systolic pressure $P_{sid}$ in the vessel 1, that is, $P_m = P_{sid}$ and continues to rise, the amplitudes of the pulse waves 3 start decreasing, which evidences of an incomplete opening of the major arterial vessel 1 under examination in the systolic phase, since the pressure $P_m$ in the cuff already gets as high as to prevent the process. With the pressure in the cuff varying linearly, the systolic portions of the pulse waves 3 are arranged in the straight line FK of the systolic region EFKL of the oscillometric curve 4.

When the pressure $P_m$ in the cuff reaches the maximum systolic pressure $P_{max}$, the arterial vessel 1 closes, blood flow along it ceases, the pulse waves 3 caused by blood strokes against the proximal cuff edge are stabilized, their amplitude stops to be diminished rapidly, and the systolic portions thereof "fall upon" the straight line KL in the systolic region EFKL of the oscillometric curve 3.

The thus-obtained signs of arterial pressure indicated with the letters B, C, F, and K in the curve 3, are projected onto the curve 2 characteristic of a linear variation of the rising pressure in the cuff to obtain the arterial pressure value at the points a, be, c, and k of the projections of the signs as follows:

at the point a—the diastolic arterial pressure $P_m$;
at the point b—the mean dynamic arterial pressure $P_{mean}$;
at the point c—the side systolic arterial pressure $P_{sid}$;
at the point k—the maximum systolic pressure $P_{max}$;

Next the cross-sectional area S of the major arterial vessel 1 under examination in the systolic and diastolic phase is determined against the amplitude values of the pulse waves 3 in the oscillometric curve 4. To determine the increment dS of the cross-sectional area S of the vessel 1, the amplitude Bb of the pulse wave 3 is measured at the point B between the straight lines AB and EF that bound the the diastolic and systolic regions, respectively. After this, the amplitude of pulse wave 3 at point C, between the straight lines CD and EF, which limit the diastolic and systolic regions, respectively, is measured to determine the total area dS=S of the cross-setion of the major arterial vessel 1 under examination.

Further on, to find the cross-sectional area S, the value dS, the increment of the cross-sectional area of the vessel 1 in the systolic phase, is subtracted from the sum S+dS.

Then the number of the pulse waves 3 are counted in the oscillometric curve 4 within the known period of time, thus determining the pulse rate of the patient under examination.

The remainder information is obtained due to calculations made according to the below-cited formulas of the circulation mechanics (cf., e.g., "The mechanics of the circulation" by C. G. Caro et al., Oxford, Oxford University Press, New York-Toronto, 1978):

the pulse arterial pressure dP is determined as the difference between the side systolic pressure $P_{sid}$ and the diastolic pressure $P_{min}$, that is $dP=P_{sid}-P_{min}$;

the hemodynamic stroke pressure $P_{sp}$ of blood is determined as the difference between maximum systolic pressure $P_{max}$ and the side systolic pressure $P_{sid}$, i.e., $P_{sp}=P_{max}-P_{sid}$;

the deformation ratio $\epsilon$ is determined as the ratio between the increment dS of the cross-sectional area S of the major arterial vessel 1 under examination in the systolic phase and the cross-sectional area S of the vessel 1 in the diastolic phase, i.e., $\epsilon=dS/S$;

the bulk modulus K of the major arterial vessel 1 under examination is determined as the product of the pulse pressure dP by the cross-sectional area S of the vessel 1 in the diastolic phase divided by the increment dS of the cross-sectional area of the vessel 1 in the systolic phase, that is, $K=(dP\cdot S)/dS$. The bulk modulus K of the major arterial vessel 1 under examination is in fact the reciprocal of the extensibility of the vessel, that is, $d=dS/(S\cdot dP)$.

the pulse wave velocity C is determined as the ratio between the bulk modulus K of the major arterial vessel 1 under examination and the known blood density value $\rho$ to power ½:

$$C=\sqrt{\frac{K}{\rho}}\ ;$$

the blood velocity U along the major arterial vessel 1 under examination is determined as the ratio between the pulse pressure dP and the pulse wave velocity C multiplied by the known blood density value $$\rho: U=\frac{dP}{C\cdot\rho}\ ;$$

the rate Q of blood flow long the major arterial vessel 1 under examination is determined as the product of the blood velocity U by the cross-sectional area S of the vessel 1 in the diastolic phase: $Q=U\cdot S=dP\cdot S/(C\cdot\rho)$;

Further calculations are carried out using the formulas derived by the Inventors:

the blood minute volume CO is determined as the rate Q of blood flow along the major arterial vessel 1 under examination per second multiplied by 60 seconds: $CO=Q\cdot 60$;

the systolic discharge SV of blood is determined as the value of the blood minute volume CO divided by the pulse rate $P_S$: $SV=CO/P_S$.

The values of the rate Q of blood flow, the blood minute volume CO, and the systolic discharge SV are calculated in relative units which are used in monitoring the state of the examinee's cardiovascular system in the course of repeated measurement of the hemodynamic parameters by the herein-disclosed oscillometric method. In such a case, one must neither change the amplification factor of the measuring system nor remove the pressure measuring cuff. The time-dependent changes in the afore-mentioned parameters are determined in percent of the initial measurement.

The measuring procedure is as follows. The patient is to assume the recumbent position, whereupon the pneumatic vessel-constricting pressure cuff is applied onto one of his limbs, the measuring system of the device is switched on, and the oscillometric curve 4 of the arterial pulse registered. Then the curve thus obtained is analyzed and the parameters Q, CO, and SV are calculated and the obtained values of Q, CO, and SV are adopted to be 100% each. Further on, with the patient continuing to be in the recumbent position and without removing or relocating the measuring cuff and without changing the amplification factor of the measuring system, the patient is given a hypotensive drug, after which the oscillometric curve 4 is registered once more, and analyzed, the values of Q, Co, and SV are calculated, and a difference in percent between the initial and second measurements is determined. It is by the changes in the values and in the absolute values measured that one can judge of the efficacy of the medicinal agents administered.

The aforedescribed law of development of the oscillometric curve 4 of the arterial pulse refers to the mode of pressure $P_m$ rise in the cuff. Under the condition of reduced pressure $P_m$ in the cuff all the processes proceeding in the vessel 1 during formation of the oscillometric curve 4 run in a reverse sequence and hence the signs of the arterial pressure are formed in the reverse order, too. It is noteworthy that the mode of rising the pressure $P_m$ in the cuff is more preferable, since even a fast rise of the pressure $P_m$ in the cuff followed by its slow reduction proves to be a load upon the vessel under examination which modifies its tonus.

In what follows the aforedescribed method is illustrated by some specific examples of its realization.

EXAMPLE 1

Male patient N., 45 was subjected to examination using the method disclosed herein. The examination was conducted under outpatient clinic conditions with the patient in the recumbent position. The volume signals of the pulse waves expressed in an oscillometric curve were entered, through an analog-to-digital converter, into an IBM-compatible personal computer and processed according to the method disclosed herein.

Figure 2:
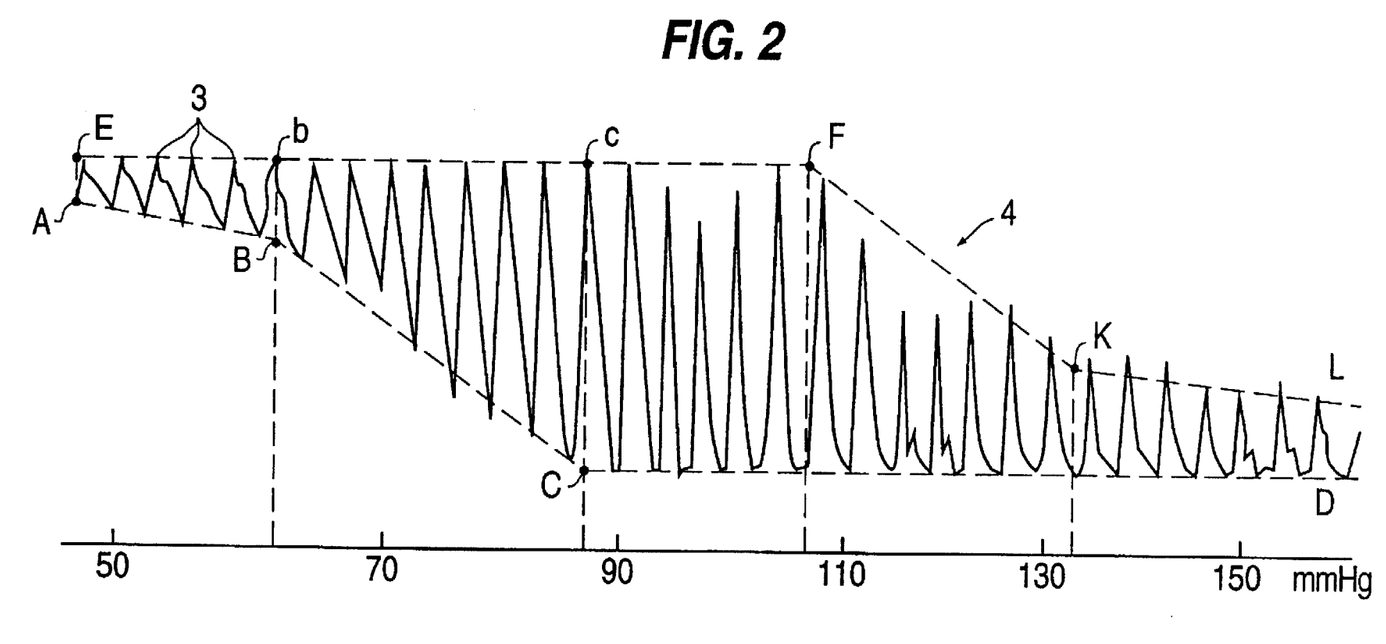
FIG. 2 presents an oscillometric curve of the arterial pulse of a particular patient under examination, obtained, according to the method disclosed herein.

FIG. 2 present an oscillometric curve of the arterial pressure taken from the patient N under examination in the mode of rising cuff pressure. The running values of the pressure measured are represented by the figures from 50 to 150 mm Hg located under the oscillometric curve.

The thus-obtained curve is approximated by the straight lines AB, BC, CD drawn through the extreme points in the diastolic region and by the straight lines EF, FK, KL in the systolic region to obtain a closed contour whose points of intersection B, C, F, K, are the signs of arterial pressure. Then the aforementioned points are projected onto the running pressure value in the cuff and the following pressure values are measured:

at the point B—the diastolic pressure $P_{min}$ equal to 61 mm Hg;

at the point C—the mean dynamic arterial pressure $P_{mean}$ equal to 87 mm Hg;

at the point F—the side systolic arterial pressure $P_{sid}$ equal to 106 mm Hg;

at the point K—the maximum systolic arterial pressure $P_{max}$ equal to 133 mm Hg.

The pulse rate counted for a known period of time equals $P_S$=65 beat/min.

Then the pulse pressure $dP=P_{sid}-P_{min}$ is calculated, equal in this particular case to dP=45 mm Hg, and the hemodynamic stroke pressure $P_{sp}=P_{max}-P_{sid}$ equal to $P_{sp}$=27 mm Hg.

Thereupon the amplitude of the pulse wave at the point B of intersection of the straight lines AB and BC is measured which corresponds to the parameter of the diastolic arterial pressure. The amount of the wave situated between the point B and the point b belonging to the straight line EF in the systolic region, is proportional to the increment dS of the cross-sectional area of the arterial vessel under examination in the systolic phase and is equal to dS=13 mm in this particular case.

The value of the pulse wave amplitude at the point C located between the diastolic and systolic regions between the points C and c is measured in a similar way. The value of the amplitude is proportional to the sum of the following areas: dS which is the increment of the cross-sectional area of the vessel under examination in the systolic phase, and S which is the cross-sectional area of the vessel in the diastolic phase. In this particular case this sum is equal to dS+S=48 mm.

The value proportional to the cross-sectional area of the major arterial vessel under examination is found as the difference between the amplitudes measured at the points C and B, respectively. In the Example discussed herein this value equals (dS+S)−(dS)=48−13=35 mm.

Next, the bulk modulus K of the major arterial vessel under examination is calculated. To convert the pressure units in mm Hg into the conventional system of units adopted in medicine for assessing the elastic properties of blood vessels use is made of a commonly known factor of 1333 for conversion of mm Hg into din/cm$^2$:

$$K = \frac{1333 \cdot dP \cdot S}{dS} = \frac{1333 \cdot 45 \cdot 35}{13} = 161,498 \text{ din/cm}^2.$$

The pulse wave velocity C is equal to C=$\sqrt{K/\rho}$=161.498/1.05=392 cm/s, where $\rho$ is blood density which normally equals approximately 1.05 kgf/m.

The blood velocity U along the vessel under examination is equal to $$u = \frac{1333 \cdot dP}{C} = \frac{1333 \cdot 45}{392 \cdot 1.05} = 145.7 \text{ cm/s}.$$

A conclusion can be drawn on the grounds of the examination performed that the principal parameters of the arterial portion of the patient's circulatory system are within the limits of norm for a sound human being.

EXAMPLE 2

Figure 3:
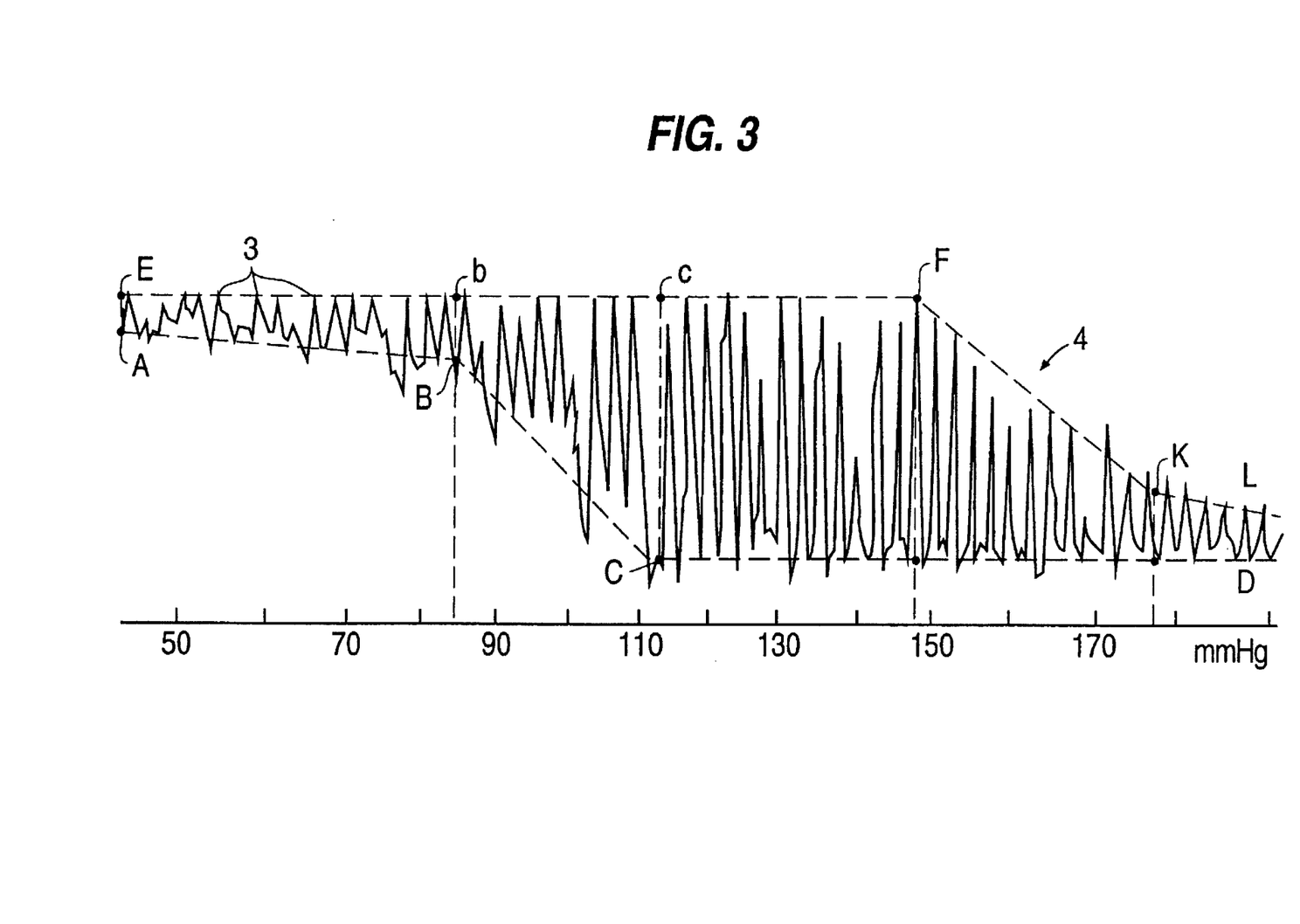
FIG. 3 illustrates an oscillometric curve obtained from another patient under examination, according to the method disclosed herein.

As a second example there can be adduced the data of a similar examination of male patient K., aged 62. FIG. 3 represents an oscillometric curve of the arterial pulse registered in the mode of rising pressure in the cuff fitted onto the patient while in the recumbent position.

Like the preceding Example, the oscillometric curve is approximated by the straight lines forming the closed contour ABCDLKFEA. The oscillometric curve thus recorded demonstrates that the patient suffers from disturbed cardiac rhythm. As a result, the pulse waves 3 have unstable amplitude, therefore one must adhere to the law of forming an oscillometric curve for determining the arterial pressure parameters by outlining the curve 4 with the contour ABCDLKFEA, through approximating some of the curve portions by straight-line segments. The running values of the cuff pressure are represented by the figures from 50–150 mm Hg situated under the oscillometric curve.

Given below are the examination results:

The diastolic arterial pressure $P_{min}$=85 mm Hg.

The means dynamic arterial pressure $P_{mean}$=112 mm Hg.

The side systolic arterial pressure $P_{sid}$=148 mm Hg.

The maximum systolic arterial pressure, $P_{max}$=178 mm Hg.

The pulse arterial pressure dP=63 mm Hg.

The hemodynamic stroke pressure $P_{sp}$=30 mm Hg.

The deformation ratio of the major arterial vessel under examination $\epsilon$=dS/S=0.32.

The bulk modulus K=262,434 dynes/cm$^2$.

The pulse wave velocity C=499.9 cm/s.

The blood velocity U=160 cm/s.

The inference can be made proceeding from both the examination results and the aspect of the oscillometric curve of the arterial pulse that the patient exhibits abnormally high numerical value of the bulk modulus and of the pulse wave velocity which point to a high rigidity of the major arterial vessel under examination. High arterial pressure values give evidence of the presence of hypertensive disease in this patient.

The reliability of measurement of arterial pressure parameters using the herein-disclosed oscillometric method was determined by comparing, under clinical conditions through contrast radiography examinations, the arterial portion of the cardiovascular system in humans exhibits a considerable spread of the arterial pressure values. Use was made of the Cournand type catheter in such examinations, which was introduced into *Arteria brachialis* along the blood stream in the vessel. The position assumed by the catheter end at the proximal cuff edge was monitored radiologically. All the calculations on the results of comparing the data of indirect and direct measurements were carried out according to the relevant U.S. standards.

Figure 4:
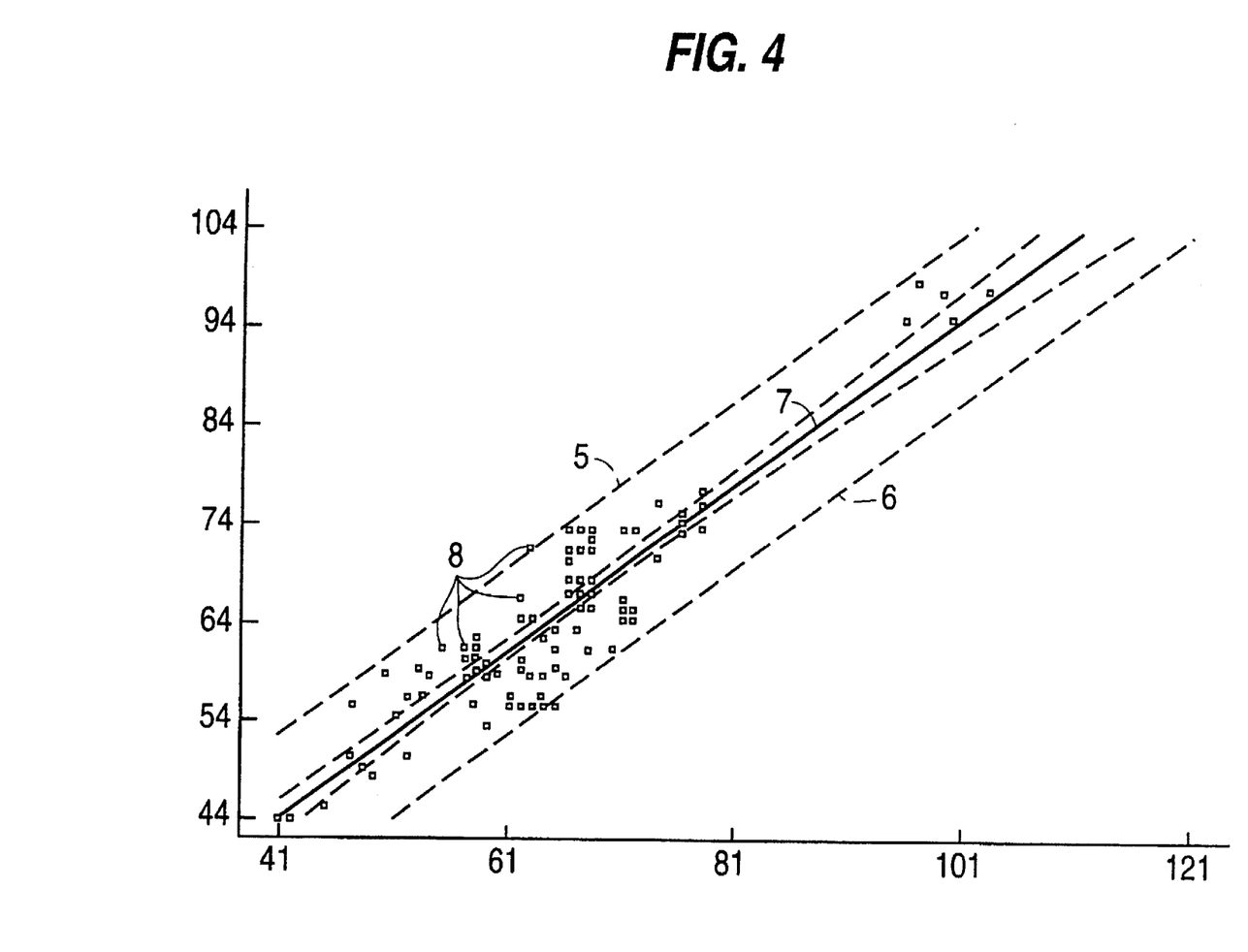
FIGS. 4, 5, 6 represent comparative data on the arterial pressure values obtained by the known method and by the method disclosed herein.

The graphic chart of FIG. 4 represents data on comparison of the value of the diastolic pressure $P_{min}$ obtained during simultaneously direct registration with the use of the catheter and by means of the oscillometric method disclosed herein. The results of the direct measurement are plotted against the X-axis, whereas the results of the oscillometric measurement are laid off on the Y-axis. Dotted lines 5 and 6 bound the zone of confidence interval, a straight line 7 being the identification line. The results of each measurement are indicated with points 8 which are 102 in number in a given measuring cycle.

As can be seen from the graphic chart the majority of the points 8 is concentrated at the identification line 7, while the remainder points are within the limits of the confidence interval. The mean measurement error d=0.535 mm Hg with the standard deviation sd=4.556 mm Hg. The comparison results demonstrate high degree of reliability of the diastolic arterial pressure values $P_{min}$ measured by the noninvasive oscillometric method disclosed herein.

Figure 5:
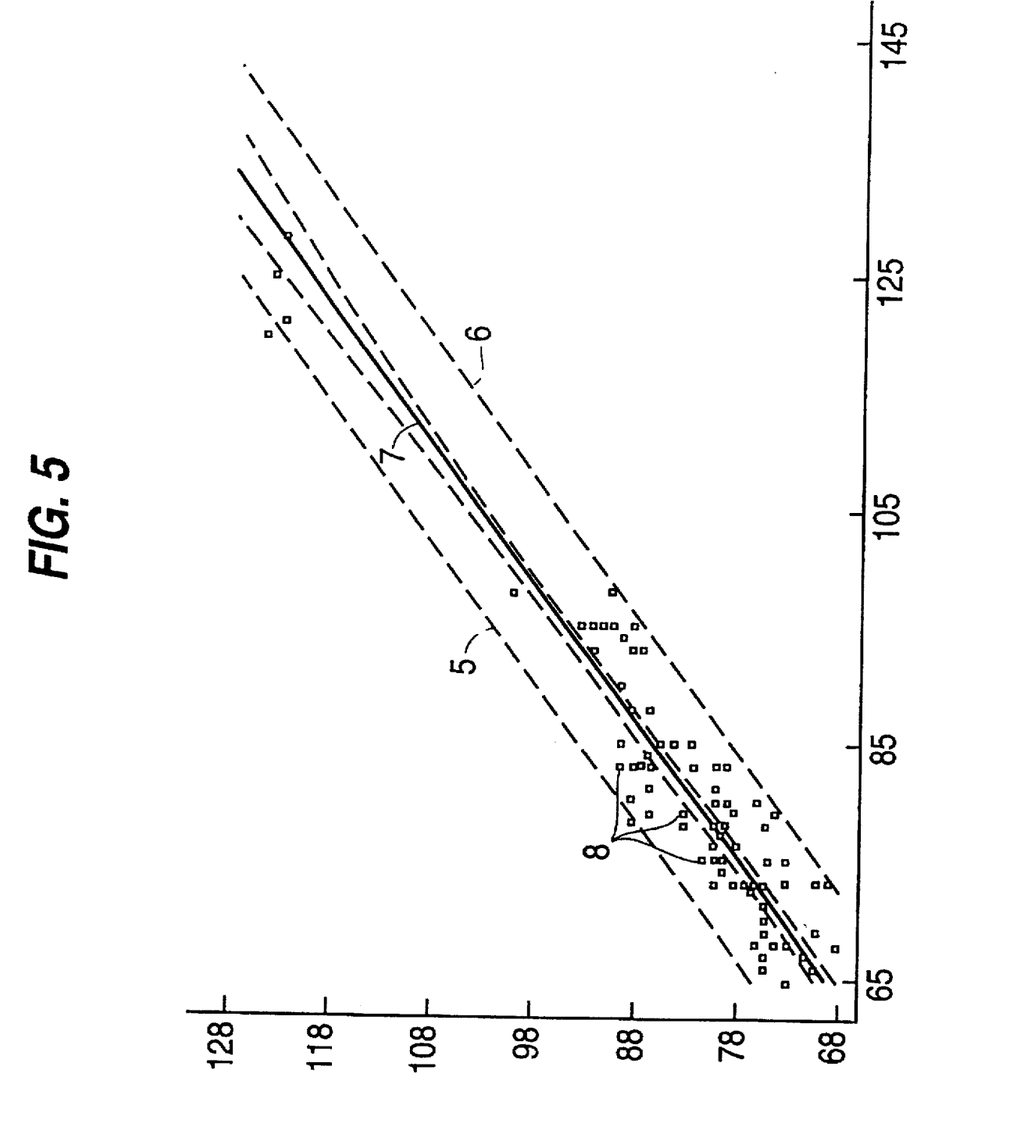
Figure 6:
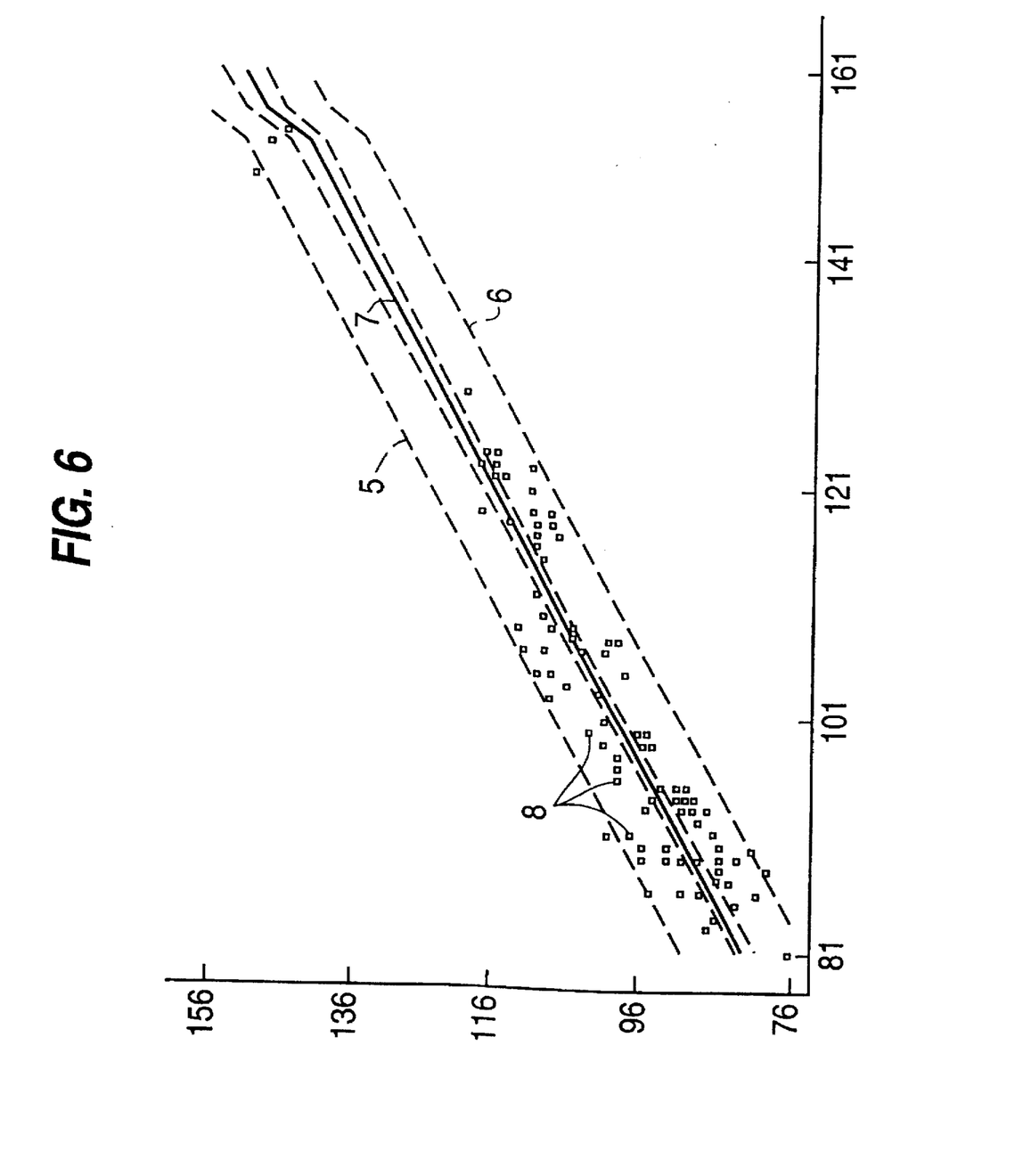

FIG. 5 represents the graphic chart of the comparative data on the values of the mean dynamic arterial pressure $P_{mean}$, and FIG. 6 is the graphic representation of comparison of the systolic pressure $P_{sid}$ obtained by the direct measuring method, and that of the side systolic pressure obtained by the oscillometric method proposed herein. Use is made in these graphs of the same symbols as in the preceding ones.

The results of comparison of the values given before presented in FIGS. 4 and 5 also demonstrate high accuracy of the received information on the values of the mean dynamic and side systolic arterial pressure with the use of the oscillometric method disclosed herein.

The method can find application in clinical practice in the cardiologic departments for diagnosis, treatment, and prevention of cardiovascular diseases, as well as the resuscitation departments for obtaining information on the effect of medicinal agents and on their administration doses. The method can successfully substitute some of the researches carried out presently and involving direct methods of catheterization of the arterial portions of the circulatory system. It also finds widespread application in preventive medical observations and under domestic conditions, as well as in practice of industrial medical establishments for diagnosis of prenosologic forms of diseases and their prevention which will substantially improve health of a population. The method is also successfully applicable in aviation and space medicine for medical support of prolonged orbital flights, for preparation to such flights, and in the postflight period.

A principal requirement imposed on the measuring system for realization of the aforedescribed oscillometric method for determining the hemodynamic parameters of the arterial portion of the circulatory system resides in linearity of its amplitude-frequency characteristic through the entire path of conversion amplification, and registration of the pulse waves 3 of the arterial pulse during forming the oscillometric curve 4 under the effect of the rising pressure 2 in the pneumatic vessel-constricting pressure cuff. In addition, the amplitude-frequency characteristic must be straight horizontal, or flat, in a frequency range of approximately from 0 to 50 Hz.

Another important requirement to the aforesaid measuring system for realization of the oscillometric method mentioned above is the linear characteristic of conversion of the arterial pulse signals along the entire path of conversion, amplification, and registration in the whole range of change of their amplitude.

One more requirement to the measuring system for realization of the oscillometric method for determining the hemodynamic parameters of the arterial portion of the circulatory system is to provide a linear increase of the pressure in the pneumatic vessel-constricting pressure cuff approximately from 0 to 300 mm Hg for about 40–60 seconds.

The aforementioned requirements are but the most important ones that must be adhered to when realizing the measuring system for carrying the proposed oscillometric method into effect. It is only in such an instance that the oscillometric curve 4 of the arterial pulse carries an information about the real changes in the lumen of the major arterial vessel 1 under examination, and formation of the oscillometric curve always obeys the regularity described above.

Figure 7:
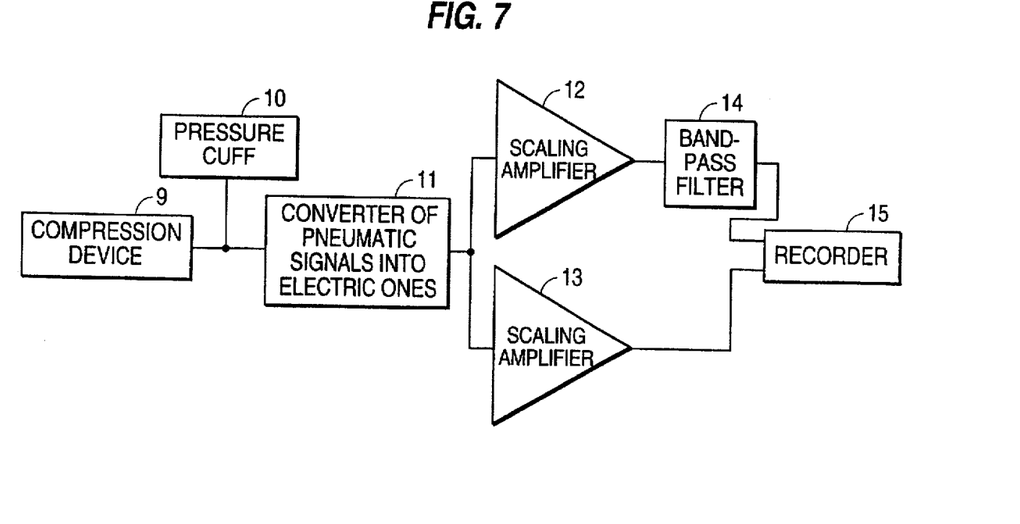
FIG. 7 depicts a block diagram of the measuring system disclosed herein.

The block diagram of one of the embodiments of the measuring system is illustrated in FIG. 7

The registration system of volume arterial oscillograms comprises series-interconnected a compression device 9 with a means for control of increasing, releasing and calibrating of the pressure in the pneumatic vessel-constricting pressure cuff 10; a converter 11 of pneumatic signals into electric ones; a scaling amplifier 12 of oscillometric signals and an additional scaling amplifier 13 of the signals of the running values of the pressure in the cuff 10; a band-pass filter 14 forming the oscillometric curve 4 of the pulse wave signals; and a recorder 15.

Used as the compression device 9 may be one of the widely known microcompressors which are made use of rather frequently in the systems of a similar character. Pressure can be raised in the cuff 10 either directly with the aid of the microcompressor or after having preliminarily pumped up the receiver to a pressure twice or thrice as high as the maximum patient's systolic arterial pressure. Operation of the microcompression device must not produce any influence upon conversion of pneumatic signals of the pulse waves 3 picked off the cuff 10, for which purpose provision is made in the air conduits for special filters (omitted in the Drawing).

It is expedient that an air stream directed to the cuff 10 be adjusted so that the pressure in the system cuff pressure converter rises at a rate of 3 to 5 mm Hg per pulse beat.

Once the measuring system has been turned on and a pressure been fed to the input of the converter 11, the pneumatic signals of the oscillometric curve 4 of the arterial pulse and the signal of the running value of the pressure in the measuring cuff 10 start to be converted in the cuff into electric signals, which are then amplified separately by the scaled amplifiers 12 and 13. The signals of the running value of the pressure in the vessel-constricting pressure cuff 10 are applied at once to the recorder 15, whereas the signals of the arterial pulse are also fed to the recorder 15, but after having passed through the band-pass filter 14. It is desirable that the signals be recorded in the orthogonal coordinates, e.g., on the mingograph available from the firm Elema, or in a personal computer.

Then the registered oscillatory signals and the pressure values in the measuring cuff are simultaneously recorded on two recorder tracks and are subjected to analysis.

A positive engineering result attainable with the aid of the method and measuring system disclosed herein resides in that the converted, amplified, and recorded signals differ virtually in nothing as for their amplitude-frequency characteristics from the true volume signals.

Figure 8:
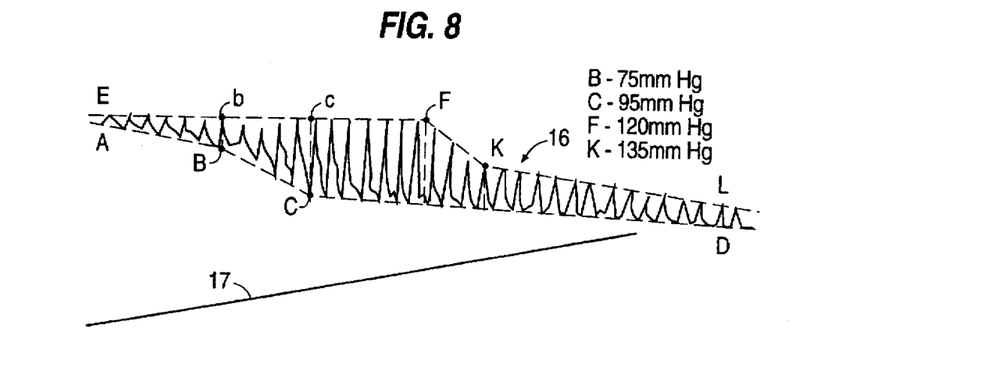
FIG. 8 shows a real oscillometric curve obtained from the patient being examined and a current value of the pressure in the pneumatic vessel-constricting pressure cuff.

FIG. 8 presents a volume arterial oscillometric curve 16 of a particular patient under examination, which has been recorded by the measuring system having the characteristics stated hereinbefore. As can be seen from said curve, its formation is accompanied by regular changes in the curve 16 as the pressure rises (a straight line 17) in the measuring cuff 10 and equalizing the latter with the instantaneous pressure values in the arterial vessel. The oscillogram acquires the aspect of a contour which can then be processed in the aforementioned method to obtain the entire set of parameters characteristic of the hemodynamic of the arterial portion of the patient's circulatory system.

We claim:

1. A method for determining principle hemodynamic parameters of an arterial portion of a circulatory system of a patient using a measuring cuff applied to a major arterial vessel of the patient and a measuring system having a linear conversion characteristic and a linear amplitude-frequency characteristic in a frequency range from approximately 0 to 50 Hz, the method comprising the steps of:

applying a linearly time-varying pressure to the major arterial vessel with the measuring cuff for a predetermined period of time, the linearly time-varying pressure being in a range from approximately 0 to 300 mm Hg;

forming a pressure curve representing the linear time-varying pressure applied to the major arterial vessel;

simultaneously measuring a plurality of amplitude values for a sequence of pulse waves of arterial pressure of the major arterial vessel using the measuring system, the measured amplitude values of the respective pulse waves representing a time-dependent change in a volume of the major arterial vessel and having a linear amplitude-frequency characteristic in a frequency range from approximately 0 to 50 Hz;

forming an oscillometric curve having a diastolic region and a systolic region based on the measured amplitude values of the sequence of pulse waves;

determining a plurality of extreme points of the oscillometric curve in the diastolic and systolic regions;

determining a plurality of lines passing through selected extreme points, the plurality of lines intersecting at points to form a closed contour;

associating the points at which the plurality of lines intersect with points on the pressure curve;

determining an absolute value of diastolic arterial pressure of the major arterial vessel based on the measured amplitude values and the associated points on the pressure curve;

determining an absolute value of a mean dynamic arterial pressure of the major arterial vessel based on the measured amplitude values and the associated points on the pressure curve;

determining an absolute value of a side systolic arterial pressure of the major arterial vessel based on the measured amplitude values and the associated points on the pressure curve; and determining an absolute value of a maximum systolic arterial pressure of the major arterial vessel based on the measured amplitude values and the associated points on the pressure curve.

2. The method according to claim 1, wherein the linear amplitude-frequency characteristics of the measuring system and of the measured amplitude values are flat.

3. The method according to claim 1, wherein the predetermined period of time the linearly time-varying pressure is applied to the major arterial vessel is from 40 to 60 seconds.

4. The method according to claim 3, wherein the step of applying the linearly time-varying pressure to the major arterial vessel includes increasing and/or decreasing the pressure during the predetermined period of time.

5. The method according to claim 1, further comprising the steps of:

determining a cross-sectional area of the major arterial vessel in a systolic phase based on the measured amplitude values of the pulse waves and the associated points on the pressure curve; and determining a cross-sectional area of the major arterial vessel in a diastolic phase based on the measured amplitude values of the pulse waves and the associated points on the pressure curve.

6. The method according to claim 5, further comprising the step of determining a pulse arterial pressure based on a difference between the side systolic arterial pressure and the diastolic arterial pressure.

7. The method according to claim 5, further comprising the step of determining a hemodynamic stroke pressure based on a difference between the maximum systolic arterial pressure and the side systolic arterial pressure.

8. The method according to claim 1, further comprising the steps of determining an estimated rate of blood flow along the major arterial vessel as a product of a value which is proportional to the cross-sectional area of the vessel in the diastolic phase and a rate of blood flow along the vessel.

9. The method according to claim 8, further comprising the step of determining a blood minute volume as a product of the estimated rate of flow and 60 seconds.

10. A method for determining principle hemodynamic parameters of an arterial portion of a circulatory system of a patient using a measuring cuff applied to a major arterial vessel of the patient and a measuring system having a linear conversion characteristic and a flat amplitude-frequency characteristic in a frequency range from approximately 0 to 50 Hz, the method comprising the steps of:

applying a linearly time-varying pressure to the major arterial vessel with the measuring cuff for a predetermined period of time, the linearly time-varying pressure being in a range from approximately 0 to 300 mm Hg;

forming a pressure curve representing the linear time-varying pressure applied to the major arterial vessel;

simultaneously measuring a plurality of amplitude values for a sequence of pulse waves of arterial pressure of the major arterial vessel using the measuring system, the measured amplitude values of the respective pulse waves representing a time-dependent change in a volume of the major arterial vessel and having a flat amplitude-frequency characteristic is a frequency range from approximately 0 to 50 Hz;

forming an oscillometric curve having a diastolic region and a systolic region based on the measured amplitude values of the sequence of pulse waves;

determining a plurality of extreme points of the oscillometric curve in the diastolic and systolic regions;

forming a plurality of lines passing through selected extreme points, the plurality of lines intersecting at points to form a closed contour;

associating the points at which the plurality of lines intersect with points on the pressure curve;

determining an absolute value of diastolic arterial pressure of the major arterial vessel based on the measured amplitude values and the associated points on the pressure curve;

determining an absolute value of a mean dynamic arterial pressure of the major arterial vessel based on the measured amplitude values and the associated points on the pressure curve;

determining an absolute value of a side systolic arterial pressure of the major arterial vessel based on the measured amplitude values and the associated points on the pressure curve;

determining an absolute value of a maximum systolic arterial pressure of the major arterial vessel based on the measured amplitude values and the associated points on the pressure curve;

determining a cross-sectional area of the major arterial vessel in a systolic phase based on the measured amplitude values of the pulse waves and the associated points on the pressure curve; and determining a cross-sectional area of the major arterial vessel under examination in a diastolic phase based on the measured amplitude values of the pulse waves and the associated points on the pressure curve.

11. The method according to claim 10, wherein the measured amplitude value of the pulse wave on which the diastolic arterial pressure is based is proportional to an incremental cross-sectional area of the major arterial vessel in the systolic phase.

12. The method according to claim 10, wherein the measured amplitude value of the pulse wave on which the mean dynamic arterial pressure is based is proportional to a sum of the cross-sectional areas of the major arterial vessel in the systolic and diastolic phases;

the method further comprising the step of subtracting the incremental cross-sectional area of the major arterial vessel in the systolic phase from a cross-sectional area of the major arterial vessel in the systolic phase to obtain the cross-sectional area of the major arterial vessel in the diastolic phase.

13. A method for determining principle hemodynamic parameters of an arterial portion of a circulatory system of a patient using a measuring cuff applied to a major arterial vessel of the patient and a measuring system associated with the measuring cuff, the measuring system having a linear conversion characteristic and a flat amplitude-frequency characteristic in a frequency range from approximately 0 to 50 Hz, the method comprising the steps of:

applying a linearly time-varying pressure to the major arterial vessel with the measuring cuff, the linearly time-varying pressure being in a range approximately from 0 to 300 mm Hg;

forming a pressure curve representing the linear time-varying pressure applied to the major arterial vessel;

simultaneously measuring a plurality of amplitude values for a sequence of pulse waves of arterial pressure of the major arterial vessel using the measuring system, the measured amplitude values of the respective pulse waves representing a time-dependent change in a volume of the major arterial vessel and having a flat amplitude-frequency characteristic in a frequency range from approximately 0 to 50 Hz;

storing the measured amplitude values;

forming an oscillometric curve having a diastolic region and a systolic region based on the measured amplitude values of the sequence of pulse waves;

determining a plurality of extreme points of the oscillometric curve in the diastolic and systolic regions;

determining a plurality of lines passing through selected extreme points, the plurality of lines intersecting at points to form a closed contour;

associating the points at which the plurality of lines intersect with points on the pressure curve;

determining an absolute value of diastolic arterial pressure of the major arterial vessel based on the measured amplitude values and the associated points on the pressure curve;

determining an absolute value of a mean dynamic arterial pressure of the major arterial vessel based on the measured amplitude values and the associated points on the pressure curve;

determining an absolute value of a side systolic arterial pressure of the major arterial vessel based on the measured amplitude values and the associated points on the pressure curve;

determining an absolute value of a maximum systolic arterial pressure of the major arterial vessel based on the measured amplitude values and the associated points on the pressure curve; and subtracting a value of an incremental cross-sectional area of the major arterial vessel in the systolic phase from the total value of the cross-sectional areas of the vessel in the systolic and diastolic phases to obtain the cross-sectional area of the vessel in the diastolic phase.

14. The method according to claim 13, further comprising the step of determining a deformation ratio of the major arterial vessel as a ratio between the incremental cross-sectional area of the vessel in the systolic phase and a cross-sectional area of the vessel in the diastolic phase.

15. The method according to claim 13, further comprising the step of determining a bulk modulus of the major arterial vessel as a ratio of the product of the pulse arterial pressure multiplied by the cross-sectional area of the vessel in the diastolic phase and the incremental cross-sectional area of the vessel in the systolic phase.

16. The method according to claim 15, further comprising the step of determining a velocity of a pulse wave along the major arterial vessel as a ratio between the bulk modulus of the vessel and a blood density value to a ½ power.

17. The method according to claim 16, further comprising the step of determining a velocity of blood along the major arterial vessel as a ratio between the value of the pulse arterial pressure and the value of the pulse wave velocity multiplied by the blood density value.

18. A measuring system for determining hemodynamic parameters of an arterial portion of a circulatory system of a patient, comprising:

a pneumatic vessel-constricting pressure cuff which is adapted to be applied to a major arterial vessel of the patient;

a compression device for generating a pneumatic pressure, the pneumatic pressure generated by the compression device being coupled to the pressure cuff for increasing a pneumatic pressure of the pressure cuff;

a converter for converting the pneumatic pressure of the pressure cuff to output electrical signals corresponding to a running pneumatic pressure of the pressure cuff and of a pneumatic pressure representing pulse waves of arterial pressure, the converter having a linear conversion characteristic and a flat amplitude-frequency characteristic in a frequency range from approximately 0 to 50 Hz;

an amplifier for scaling the output electrical signals of the converter, the scaling amplifier having a linear characteristic of conversion and a flat amplitude-frequency characteristic in a frequency range from approximately 0 to 50 Hz;

a filter for filtering the output electric signal of the converter corresponding to the pulse waves of arterial pulse pressure, the filter having a flat amplitude-frequency characteristic in a frequency range from approximately 0 to 50 Hz, said filter transmitting filtered electrical signals corresponding to volume oscillometric data for said arterial portion derived from the output electric signal; and a memory for storing the scaled electrical signals corresponding to the running pneumatic pressure of the pressure cuff and the filtered electrical signals corresponding to the volume oscillometric data of the arterial portion of the circulatory system of the patient.

19. The measuring system according to claim 18, wherein the amplifier includes a second amplifier, coupled between the converter and the memory, for scaling the electrical signal corresponding to the pneumatic pressure of the compression device.

20. Apparatus for determining a hemodynamic parameter of an arterial portion of the circulatory system of a patient, said apparatus comprising:

a pressure cuff for applying pressure to a portion of a patient's body and an arterial blood vessel therein responsive to pressurization of said cuff;

pressurizing apparatus pressurizing said pressure cuff, said pressurizing apparatus being operatively associated with said cuff and varying the pressure applied to said cuff substantially linearly with respect to time;

a sensor operatively associated with the cuff and generating a pressure signal corresponding to the pressure in said cuff;

a signal processing system having an input and an output, said input receiving said pressure signal, said signal processing system generating first and second signals and transmitting said first and second signals through said output, said first signal corresponding to the pressure in the cuff, and the second signal corresponding to a volume oscillometric signal for the arterial portion derived from said pressure signal;

a recording device receiving said first and second signals and recording said signals in a form permitting determination of the amount of pressure applied to the cuff at a point in time identified from the second signal.

21. The invention according to claim 20 and said pressurizing apparatus applying linearly increasing pressure to the cuff.

22. The invention according to claim 21 and said pressurizing apparatus varying the pressure in a range of from about 0 mm Hg to a pressure sufficient to cause compression of the artery.

23. The invention according to claim 20 and said pressurizing apparatus applying linearly decreasing pressure to the cuff.

24. The invention according to claim 23 and said pressurizing apparatus varying the pressure in a range of from about 0 mm Hg to a pressure sufficient to cause compression of the artery.

25. The invention according to claim 20 and said signal processing system having a linear conversion characteristic.

26. The invention according to claim 20 and said signal processing system having a substantially straight horizontal amplitude-frequency characteristic in a frequency range from about 0 to 50 Hz.

27. The invention according to claim 20 and said signal processing system including a signal processor operatively associated with said output and transmitting said second signal to said output, said signal processor including a filter passing a band of frequencies ranging from about 0 Hz of a signal transmitted thereto as filtered output and having a substantially straight horizontal amplitude-frequency characteristic in said band of frequencies;

said signal processor transmitting said pressure signal or a signal derived from said pressure to said filter and transmitting said filtered output or a signal derived therefrom to the output as said second signal.

28. The invention according to claim 27 and said filter passing a band of frequencies in a range of about 0 to 50 Hz.

29. The invention according to claim 27 and said signal processor including an amplifier amplifying said pressure signal before transmitting said pressure signal to said filter.

30. The invention according to claim 27 and said signal processing system including an amplifier for amplifying said pressure signal and transmitting said amplified signal to said output as said first signal.

31. The invention according to claim 27 and said signal processing system being an analog circuit.

32. The invention according to claim 20 and said recording device comprising a computer preserving said first and second signals.

33. The invention according to claim 20 and said recording device comprising a recording apparatus preserving said first and second signals in graphic form.

34. An apparatus as claimed in claim 20 wherein said output of said signal processing system comprises two separate output lines each transmitting a respective one of said first and second signals.

35. Apparatus for determining a hemodynamic parameter of an arterial portion of the circulatory system of a patient, said apparatus comprising:

a pressure cuff for applying pressure to a portion of a patient's body and an arterial blood vessel therein responsive to pressurization of said cuff;

pressurizing apparatus pressurizing said pressure cuff, said pressurizing apparatus being operatively associated with said cuff and varying the pressure applied to said cuff substantially linearly with respect to time;

a sensor operatively associated with the cuff and generating a pressure signal corresponding to the pressure in said cuff;

a signal processing system receiving said pressure signal and generating first and second signals, and having an output transmitting said first and second signals therefrom, said first signal corresponding to the pressure in the cuff, and the second signal corresponding to a volume oscillometric signal derived from said pressure signal;

a recording device receiving said first and second signals and recording said signals in a form permitting determination of the amount of pressure applied to the cuff at a point in time identified from the second signal;

said pressurizing apparatus applying linearly increasing pressure to the cuff; and said pressurizing apparatus applying said pressure in a range of from approximately 0 mm Hg to a pressure adequate to cause the second signals to have an increase in amplitude relative to the amplitude thereof when the pressurizing apparatus applies pressure to the cuff at approximately the lower limit of said range of pressure.

36. The invention according to claim 35 and said pressurizing apparatus applying said pressure in a range of from approximately 0 mm Hg to a pressure to cause the systolic peak values of the second signal to decrease from the substantially constant value thereof when the pressurizing apparatus applies pressure to the cuff at the lower limit of said range of pressure.

37. The invention according to claim 35 and said pressurizing apparatus applying said pressure in a range of from approximately 0 mm Hg to a pressure adequate to cause the diastolic minimum values of the second signal to reach a substantially constant value after a decrease from an initial value when the pressurizing apparatus applies pressure to the cuff at approximately the lower limit of said range of pressure.

38. The invention according to claim 35 and said pressurizing apparatus applying said pressure in a range of from approximately 0 mm Hg to a pressure adequate to cause a reduction in the slope of descent of the systolic peak values of the second signal.

39. Apparatus for determining a hemodynamic parameter of an arterial portion of the circulatory system of a patient, said apparatus comprising:

a pressure cuff for applying pressure to a portion of a patient's body and an arterial blood vessel therein responsive to pressurization of said cuff;

pressurizing apparatus pressurizing said pressure cuff, said pressurizing apparatus being operatively associated with said cuff and varying the pressure applied to said cuff substantially linearly with respect to time;

a sensor operatively associated with the cuff and generating a pressure signal corresponding to the pressure in said cuff;

a signal processing system receiving said pressure signal and generating first and second signals, and having an output transmitting said first and second signals therefrom, said first signal corresponding to the pressure in the cuff, and the second signal corresponding to a volume oscillometric signal derived from said pressure signal;

a recording device receiving said first and second signals and recording said signals in a form permitting determination of the amount of pressure applied to the cuff at a point in time identified from the volume oscillometric signal; and said recording device preserving said first and second signals in a form which permits determination of the pressure applied to said cuff approximately at one of the following points in time:

a) the point in time at which the amplitude of the pulse of the volume oscillometric signal began to increase;

b) the point in time at which the diastolic minimum of the volume oscillometric signal ceased to decline;

c) the point in time at which the systolic peaks of the volume oscillometric signal started to decline; or d) the point in time at which the generally linear rate of decline of the systolic peaks of the volume oscillometric signal changed to a slower linear rate of decline.

40. A method for determining hemodynamic parameters of a patient's arterial system, said method comprising:

applying a pressure cuff to said patient;

applying pressure to said cuff which varies generally linearly with respect to time, said pressure applied being in a range of from about 0 mm Hg to a pressure sufficient to cause said cuff to compress an artery of said patient;

sensing the pressure in said cuff and generating a pressure signal corresponding to said pressure in said cuff;

processing said pressure signal, including preparing from said pressure signal a first signal corresponding to the pressure in said cuff at a given point in time and deriving a second signal which corresponds to the oscillometric volume data for said arterial portion at said point in time; and storing said first and second signals in a form that permits a correlation of a point in time of an event detected from the second signal with the value of the first signal at approximately said point in time.

41. The method according to claim 40 and said applying of varying pressure being an application of substantially linearly increasing pressure to said cuff.

42. The method according to claim 41 and said deriving of said second signal including passing said pressure signal through a circuit which includes a filter which permits passage only of frequency signals in a range beginning at approximately 0 Hz and which circuit has substantially linear conversion characteristic and a substantially flat amplitude-frequency characteristic in said range of frequencies.

43. The method according to claim 42 and said storing being accomplished using a computer storing said signals.

44. The method according to claim 41 and said deriving of said second signal including passing said pressure signal through a circuit which includes a filter which permits passage only of frequency signals in a range of approximately 0 to approximately 50 Hz.

45. The method according to claim 41 and said deriving of said second signal including passing said pressure signal through a circuit which includes a filter which permits passage only of frequency signals in a range of approximately 0 to approximately 50 Hz, said circuit having a flat horizontal amplitude-frequency characteristic in said range.

46. A method for determining hemodynamic parameters of a patient's arterial system, said method comprising:

applying a pressure cuff to said patient;

applying pressure to said cuff which varies generally linearly with respect to time, said pressure applied being in a range of from about 0 mm Hg to a pressure sufficient to cause said cuff to compress an artery of said patient;

sensing the pressure in said cuff and generating a pressure signal corresponding to said pressure;

processing said pressure signal, including preparing from said pressure signal a first signal corresponding to the pressure in said cuff at a given point in time and deriving a second signal which represents the value of the oscillometric volume curve at said point in time; and storing said first and second signals in a form that permits a correlation of an event detected from the second signal with the value of the first at the time of that event; and determining at least one of the following hemodynamic parameters as the pressure in said cuff at the time of the respective volume oscillometric event:
a) the diastolic pressure, based on the point in time at which the amplitude of the pulse of the volume oscillometric signal began to increase;
b) the mean dynamic arterial pressure, based on the point in time at which the diastolic minimum of the volume oscillometric signal ceased to decline;
c) the side systolic pressure, based on the point in time at which the systolic peaks of the volume oscillometric signal started to decline; or
d) the maximum systolic pressure, based on the point in time at which the generally linear rate of decline of the systolic peaks of the volume oscillometric signal changed to a slower linear rate of decline.

* * * * *